United States Patent [19]
Nakajima et al.

[11] Patent Number: 5,959,183
[45] Date of Patent: Sep. 28, 1999

[54] CYTOPLASMIC MALE STERILITY DNA FACTOR AND UTILIZATION THEREOF

[75] Inventors: Yuki Nakajima, Irvine, Calif.; Toshiya Yamamoto, Ibaraki; Kenji Oeda, Kyoto, both of Japan

[73] Assignee: Sumitomo Chemical Company, Limited, Osaka, Japan

[21] Appl. No.: 08/928,419

[22] Filed: Sep. 12, 1997

[30] Foreign Application Priority Data

Sep. 13, 1996 [JP] Japan .................................. 8-243201

[51] Int. Cl.$^6$ ................ A01H 5/00; A01H 1/02; C12N 15/29; C12N 15/82
[52] U.S. Cl. ................ 800/303; 800/274; 800/278; 800/298; 435/6; 435/252.3; 435/320.1; 435/419; 435/468; 536/23.6
[58] Field of Search .................. 536/23.6; 435/252.3, 435/320.1, 419, 468, 6; 800/278, 274, 298, 303

[56] References Cited

U.S. PATENT DOCUMENTS

| | | | |
|---|---|---|---|
| 5,356,799 | 10/1994 | Fabijanski et al. | 435/172.3 |
| 5,650,559 | 7/1997 | Akamatsu et al. | 800/220 |

FOREIGN PATENT DOCUMENTS

| | | |
|---|---|---|
| 6-75198A1 | 10/1995 | European Pat. Off. . |
| 9401153 | 2/1995 | Netherlands . |
| WO86 07379 | 12/1986 | WIPO . |
| WO92 05251 | 4/1992 | WIPO . |

OTHER PUBLICATIONS

Krishnasamy et al. (1994), Organ–specific reduction in the abundance of a mitochondrial protein accompanies fertility restoration in cytoplasmic male–sterile radish, Plant Molecular Biology 26:935–946.
Walters et al. (1992), Protoplast fusion–derived Ogura male sterile cauliflower with cold tolerance, Plant Cell Report 10:624–628.
Chemical Abstract No. XP–002076886.
Chemical Abstract No. XP–002076887.
Chemical Abstract No. XP–002076888.
S. Krishnasamy et al., Current Genetics, 24:156–163 (1993).
S. Bonhomme et al., Mol. Gen. Genet., 235:340–348 (1992).
M. Spassova et al., Plant Molecular Biology, 26:1819–1831 (1994).
J. Ronfort et al., Theor. Appl. Genet., 91:150–159 (1995).
R. Scheike et al., Theor. Appl. Genet., 83:419–427 (1992).
H. Kanzaki et al., Jpn. J. Genet., 66:719–724 (1991).
Ronfort et al. Theor. Appl. Genet. 91(1):150–159, 1995.
Kanzaki et al. Jpn. J. Genet. 66(6):719–724, 1991.
Spassova et al. Plant Mol. Biol. 26(6):1819–1831, 1994.
Laver et al. Plant J. 1(2):185–193, 1991.

*Primary Examiner*—David T. Fox
*Attorney, Agent, or Firm*—Birch, Stewart, Kolasch & Birch, LLP

[57] ABSTRACT

There is provided a cytoplasmic male sterility DNA factor, a method of discrimination which enables confirmation of the cytoplasmic male sterility in a short time.

8 Claims, 3 Drawing Sheets ically male sterility DNA factor and a method of discriminating of a plant having the same.

CYTOPLASMIC MALE STERILITY DNA FACTOR AND UTILIZATION THEREOF

FIELD OF THE INVENTION

The present invention relates to a cytoplasmic male sterility DNA factor and a method of discriminating of a plant having the same.

A desirable cytoplasmic male sterility line as a parent line for producing a useful F1 hybrid seed has been obtained by a conventional process of repeated crossing of pollen from a cultivar to which sterilization is desired with a plant providing cytoplasmic male sterility for the purpose of replacing the nucleus of the latter with that of the former cultivar having desired traits to be introduced. Alternatively, asymmetrical cell fusion has been used for the same purpose.

Since, however, it required laborious work and took a long time to confirm the fertility of flowers of respective candidate plant provided by each crossing or cell fusion, there has been a strong demand for checking cytoplasmic male sterility traits in a short time without a time loss of flower breeding.

Under such circumstances, the present inventors have conducted extensive researches and, as a result, discovered a cytoplasmic male sterility DNA factor specifically expressed in a male sterility cytoplasm, successfully isolated the said DNA, and found a method to check the presence of the same gene, whereby completing the present invention.

SUMMARY OF THE INVENTION

The present invention provides:
1. A DNA comprising a nucleotide sequence selected from the group consisting of:
    (a) a nucleotide of 171 bp characterized by a restriction map shown by FIG. 1 and has restriction sites, HinfI (5 bp), MboI (24 bp), MboI (43 bp) and HapII (122 bp);
    (b) a nucleotide sequence shown by SEQ ID NO: 1;
    (c) a nucleotide sequence encoding the amino acid sequence depicted in SEQ ID NO:2; and
    (d) a nucleotide sequence hybridizing with a nucleotide sequence of (b) or (c),
2. A method of discriminating a plant containing a cytoplasmic male sterility DNA factor as defined above, which comprises:
    (a) carrying out a PCR-amplification of a genomic DNA of a plant using, as a primer, an oligonucleotide which can amplify a cytoplasmic male sterility DNA factor as defined above or a part of it or a DNA containing said DNA or an equivalent thereof,
    (b) separating the amplified genomic DNA by electrophoresis, and then
    (c) visually detecting the amplified genomic DNA (hereinafter, this method is referred to as the method of discrimination of the present invention),
3. A method of discriminating a plant containing a cytoplasmic male sterility DNA factor as defined above, which comprises: conducting Southern or Northern hybridization on a genomic DNA or RNA of a plant as sample for analysis using, as a probe, a cytoplasmic male sterility DNA factor as defined above or an equivalent thereof (hereinafter, this method is referred to as the method of discrimination through hybridization of the present invention); and
4. A DNA comprising a nucleotide sequence selected from the group consisting of:
    (a) a nucleotide sequence of 651 bp and having a restriction map as depicted in FIG. 2 and has restriction sites, NdeI (80 bp), EcoRI (117 bp), MvaI (152 bp), AccIII (165 bp), NspV (249 bp), SalI (275 bp), BamHI (300 bp) and HinfI (485 bp);
    (b) a nucleotide sequence shown by SEQ ID NO: 3;
    (c) a nucleotide sequence encoding the amino acid sequence depicted in SEQ ID NO:4; and
    (d) a nucleotide sequence hybridizing with a nucleotide sequence of (b) or (c).

The present invention further provides a plasmid containing the cytoplasmic male sterility DNA factor and a method conferring the cytoplasmic male sterility to a plant, plant cell or microorganisms by transfecting the plant, plant cells or microorganisms with the plasmid, and a plant, plant cells or microorganisms into which said cytoplasmic male sterility is introduced and expressing the same.

Figure 1:
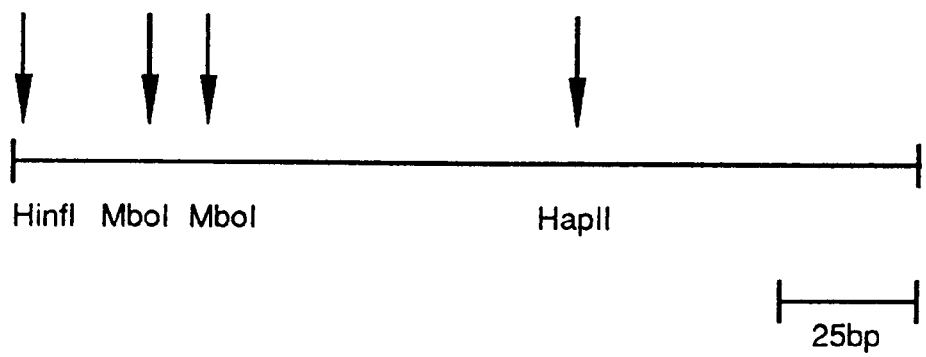
FIG. 1 shows restriction map representing the structure of a male sterility DNA factor of the present invention, wherein restriction sites, HinfI (5 bp), MboI (24 bp), MboI (43 bp) and HapII (122 bp) are indicated by arrows.

In the drawing, cultivar No. 1 denotes "MS-1", cultivar No. 2 denotes "MS-2", cultivar No. 3 denotes "Kokubusenkoudaicho", cultivar No. 4 denotes "Imperator", cultivar No. 5 denotes "Nagafutorikintoki", cultivar No. 6 denotes "Koizumirisougosun", and cultivar No. 7 denotes "Kikuyogosun".

Figure 4:
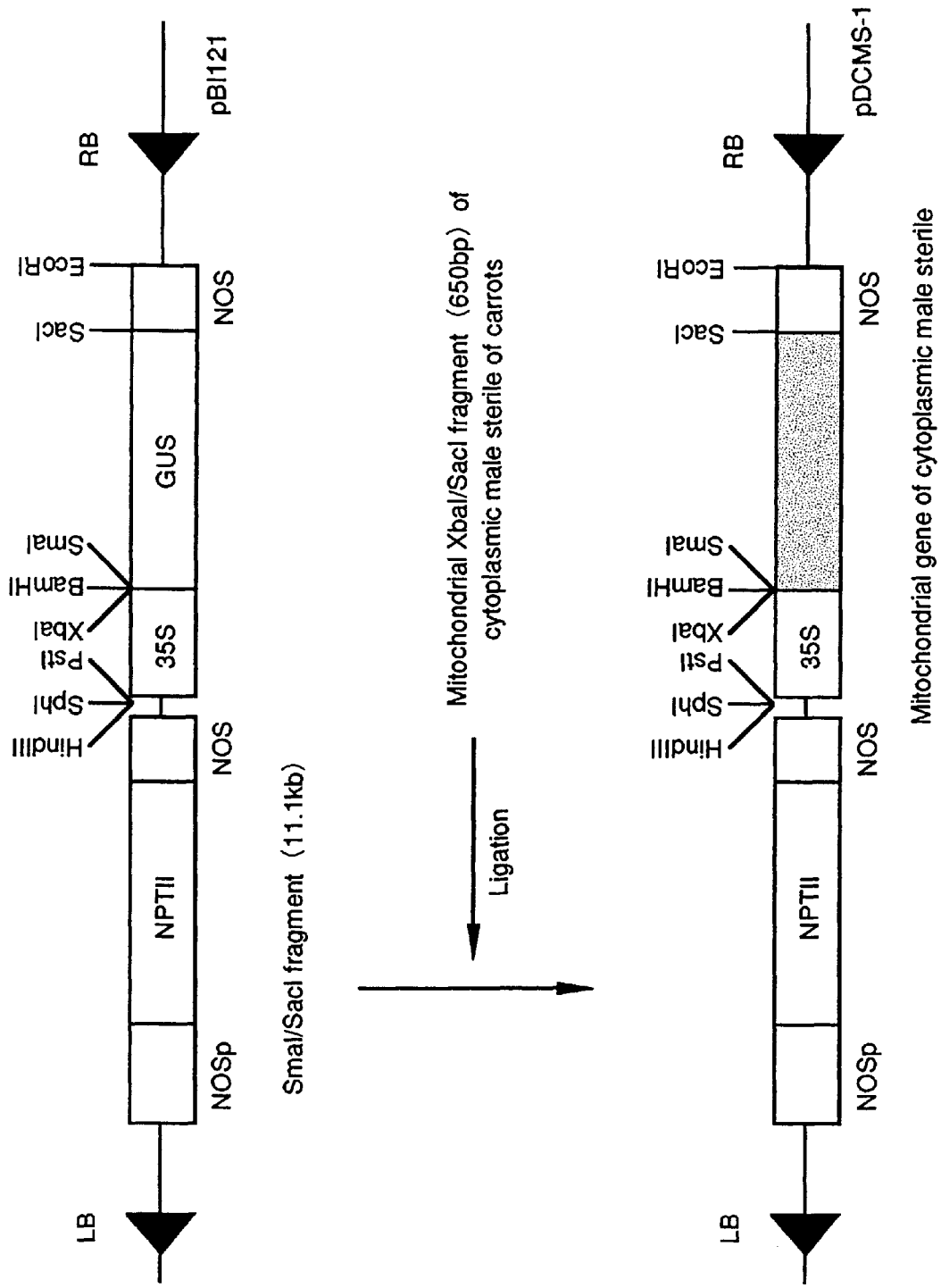

FIG. 4 shows steps for constructing pDCMS-1 which is a (sterility type) plasmid of the present invention.

DESCRIPTION OF THE PREFERRED EMBODIMENTS

The present invention will be described in more detail.

First, a description will be made to a DNA comprising a nucleotide sequence selected from the group consisting of:
    (a) a nucleotide of 171 bp characterized by a restriction map shown by FIG. 1 and has restriction sites, HinfI (5 bp), MboI (24 bp), MboI (43 bp) and HapII (122 bp),
    (b) a nucleotide sequence shown by SEQ ID NO: 1;
    (c) a nucleotide sequence encoding the amino acid sequence depicted in SEQ ID NO:2; and
    (d) a nucleotide sequence hybridizing with a nucleotide sequence of (b) or (c).

The nucleotide is a cytoplasmic male sterility DNA factor and is a part of a gene which is specifically expressed in a male sterility cytoplasm and has a function of conferring male sterility, it also may be ligated to a mitochondria gene to express male sterility.

Said DNA factor is a DNA fragment of 171 bp, characterized by a restriction map shown by FIG. 1 and has restriction sites for HinfI (5 bp), MboI (24 bp), MboI (43 bp) and HapII (122 bp). It includes the nucleotide sequence shown in SEQ ID NO: 1 and the said DNA includes a nucleotide sequence hybridizing with either a nucleotide sequence shown by SEQ ID NO: 1 or a nucleotide sequence encoding the amino acid sequence as depicted in SEQ ID NO:2.

The DNA factor can be obtained by using, as a template, a mitochondrial genomic DNA extracted from a tissue such as a leaf, stem or the like or cultured cells for a carrot stain having cytoplasmic male sterility, for example, a carrot strain "493S", "2566A", "9304A" or the like.

The extraction of the genomic gene is carried out by a method, for example, described in Methods of Experiment in Molecular Biology for Plants, Translation Supervised by S. Toyama, Published by Maruzen, or using a commercially available plant DNA extraction kit, for example, Isoplant (Wako Pure Chemical Industries, Ltd.) or the like.

The extracted genomic gene is used as a template in a PCR process (for example, at an annealing temperature of 55° C., in 30 cycles) using the following oligonucleotide primers:

5' TATGACTCCTTCTTTCACTT 3' (SEQ ID NO:9) and

5' CTATTTTGAATTTTTTTCCGT 3' (SEQ ID NO:10)

to amplify the gene DNA.

The amplified DNA is further subjected to electrophoresis, for example, on agarose gel of about 1.5%. The DNA fragment of 171 bp is isolated by excising from the agarose gel, and the obtained fragment is purified with a commercially available kit (for example, one manufactured by Bio Rad).

The fragment may be further cloned by a method described in a kit with a commercially available plasmid vector (for example, pCRII manufactured by Invitrogen) to obtain a plasmid containing said cytoplasmic male sterility DNA factor (the plasmid of the present invention) and a microorganism carrying said plasmid (the microorganism of the present invention). The plasmid of the present invention is useful for introducing the male sterility DNA factor of the present invention into a plant cell or a plant having a cytoplasmic fertility type mitochondria gene.

Next, a description will be made to a method of discriminating a plant containing the cytoplasmic male sterility DNA factor as defined above, which comprises:

(a) carrying out a PCR-amplification of a genomic DNA of a plant using, as a primer, an oligonucleotide which can amplify the cytoplasmic male sterility DNA factor or a part of it or a DNA containing said DNA or an equivalent thereof, (b) separating the amplified genomic DNA by electrophoresis, and then (c) visually detecting the amplified genomic DNA.

The primer to be used in the method of discrimination of the present invention is not particularly limited insofar as it is an oligonucleotide which can amplify the cytoplasmic male sterility DNA factor or a nucleotide sequence shown by SEQ ID NO: 1 or a part of it or a DNA containing said DNA or an equivalent of them and includes oligonucleotides having usually about 15 or more nucleotides. Preferably, the oligonucleotide has 20 or more and 30 or less nucleotides.

Examples of the primer oligonucleotide which can amplify the cytoplasmic male sterility DNA factor shown by SEQ ID NO: 1 are:

5' TATGACTCCTTCTTTCACTTT 3' (SEQ ID NO:11) and

5' CTATTTTGAATTTTTTTCCGT 3' (SEQ ID NO:12)

Examples of the primer which can amplify a part of cytoplasmic male sterility DNA factor shown by SEQ ID NO: 1 or a DNA containing said DNA are:

5' CTGGATCGACGAAACAGTCC 3' (SEQ ID NO:13) and

5' TAAAAATGGAGCGAGAAGAA 3' )SEQ ID NO:14).

Examples of the primer which can amplify an equivalent of a cytoplasmic male sterility DNA factor shown by SEQ ID NO: 1 or a part of it or a DNA containing said DNA are:

5' ATGCCTCAACTGGATAAATT 3' (SEQ ID NO:15) and

5' CTATTTTGAATTTTTTTCCGT 3' (SEQ ID NO:12).

The expression "an equivalent of them (a cytoplasmic male sterility DNA factor which is a nucleotide sequence shown by SEQ ID NO: 1 or a part of it or a DNA containing said DNA)" used herein means a cytoplasmic male sterility DNA factor having a nucleotide sequence shown by SEQ ID NO: 1 in which a single nucleotide or plural nucleotides added, deleted or replaced (i.e., a DNA factor which is a part of a gene which can be specifically expressed in a male sterility cytoplasm and which has a function of providing male sterility, for example, preferably when ligated to a mitochondria gene) and refers to a DNA which is an analogue having the same function.

The oligonucleotide used as a primer can be obtained with a commerically available automatic DNA synthesizer using, for example, β-cyanoethyl phosphoramidite process or thiophosphite process.

A plant containing the cytoplasmic male sterility DNA factor can be discriminated by amplifying a genomic DNA of the plant by a PCR process using the above described primer, separating the amplified genomic DNA by electrophoresis and visually detecting the amplified genomic DNA.

The term "PCR process (polymerase chain reaction process)" used herein refers to a process for amplifying a specific DNA utilizing a reaction in which a DNA replicating cycle including a denaturation step, an annealing step for a primer and an elongation step is repeatedly conducted and conventional procedures are described, for example, in Saiki et al., Science, 230, 1350–1354 (1985), "Protocol for Experiments in Plant PCR" Plant Cell Industry, Supplement, Supervised by Ko Shimamoto and Takuji Sasaki, Published by Shujunsha Co., Ltd., Tokyo, 1995, and the like.

The genomic DNA of a plant to be applied as a sample in the method of discrimination of the present invention (i.e., a specimen acting as a template) can be prepared by a conventional extraction process.

Such processes for extracting a genomic DNA of a plant are described, for example, in The Newest Fundamental of Experiment in Agriculture, Edited by Department of Agriculture, Faculty of Agriculture, Tohoku University, Published by Softscience, Tokyo, 1990, "Protocol for Experiments in Plant PCR" Plant Cell Industry, Supplement, Supervised by Ko Shimamoto and Takuji Sasaki, Published by Shujunsha Co., Ltd., Tokyo, 1995, and the like.

The extraction is carried out by the following steps. A tissue such as a green leaf of a test plant is triturated in liquid nitrogen. The triturated product is treated with a cetyl trimethyl ammonium bromide (CTAB) solution, incubated and then combined with chloroform-isoamyl alcohol, followed by sufficient mixing. The aqueous layer is separated and mixed with isopropyl alcohol. The formed precipitates are collected, dissolved by adding a buffer solution containing, for example, EDTA and treated with RNase. Then, the solvent is replaced by phenol, phenol plus chloroform-isoamyl alcohol, and chloroform-isoamyl-alcohol in this order. After this replacing treatment, the genomic DNA is obtained by centrifugation.

More specifically, a mitochondrial genomic DNA, as a genimic DNA of a plant, can be prepared by, for example, a method of L. R. DeBonte et al. (Plant Mol. Biol. Rep., 3, 32–36 (1985)). The process can be carried out by the following steps. A protoplast derived from cultured cells of a test plant is subjected to cell wall destruction in a buffer solution. The destructed product is centrifuged to collect a mitochondria fraction, which is treated with DNase to remove contaminating genomic DNA. The purified mitochondria fraction is treated with a proteinase to digest the mitochondrial membrane, extracted with phenol and chloroform and the obtained mixture of mitochondria DNA and RNA is treated with RNase. Upon extraction with phenol and chloroform, a mitochondrial DNA is obtained.

The polymerase chain reaction in PCR process used in the method of discrimination of the present invention include a repeated reaction in which about 20 to about 40, preferably about 25 to about 35 times of DNA replication cycles are carried out, for example, in a buffer solution for amplification including the above described primer, a DNA polymerase, 4 kinds of nucleotides (dATP, dTTP, dCTP and dGTP) and genomic DNA of a plant and about 1.0 mM to about 4.0 mM, preferably about 1.5 mM to about 3.0 mM, magnesium chloride and the like.

Each steps in the polymerase chain reaction can be conducted in the following conditions.

The denaturation step is carried out, for example, by heating at usually about 90° C. to about 95° C., preferably about 94° C. to about 95° C., and for about 1 minute to about 3 minutes, preferably 1 minute to about 2 minutes.

The annealing step of the primer is carried out, for example, by incubating with the primer at usually about 40° C. to about 60° C., preferably about 50° C. to about 60° C., and for about 1 minute to about 3 minutes, preferably 1 minute to about 2 minutes.

As the primer, the oligonucleotide used in the present invention is used alone or in combination. The elongation step with a DNA polymerase is carried out, for example, by treating with a heat resistant DNA polymerase at usually about 70° C. to about 73° C., preferably about 72° C. to about 73° C., and for about 1 minute to about 4 minutes, preferably 2 minutes to about 3 minutes.

The heat resistant DNA polymerase includes commercially available one, for example, a heat resistant DNA polymerase manufactured by Takara Shuzo or the like.

The amplified genomic DNA obtained by the above described process is separated by conventional electrophoresis. In general, about 3% to about 20% polyacrylamide gel is suitable for separation of short DNA fractions of 1,000 bp or less and about 0.2% to about 2% agarose gel is suitable for longer DNA fractions. Preferred is about 1% to about 2% agarose gel.

The buffer solution used in electrophoresis includes Tris-phosphate (pH 7.5–8.0), Tris-acetate (pH 7.5–8.0), Tris-borate (pH 7.5–8.3) and so on. Preferred one is Tris-acetate. If necessary, EDTA or the like may be added.

Conditions for electrophoresis include, for example, a combination of 100 V and 40 minutes, 50 V and 80 minutes or the like.

Size markers include a completely hydrolyzed product of lambda DNA with restriction enzyme HindIII, such as a commercially available one manufactured by Takara Shuzo.

The visual detection of the amplified DNA in the present invention include, for example, a process in which DNA is detected by a staining-method using a phenanthridine coloring substance capable of interacting with a nucleic acid such as ethidium bromide.

In said staining method, a red band due to a complex of DNA and ethidium bromide can be detected even in the course of electrophoresis by irradiating the gel with ultraviolet rays of 254 nm, 366 nm or the like in the dark, if a coloring substance such as ethidium bromide at a final concentration of about 0.5 µg/ml is added beforehand to the buffer solution for electrophoresis. Usually, however, a red band due to a complex of DNA and ethidium bromide is detected after electrophoresis by irradiating the gel with ultraviolet rays of 254 nm, 366 nm or the like in the dark after immersing the gel in a solution of a coloring substance such as ethidium bromide for about 15 minutes to about 60 minutes.

Further, a plant containing the cytoplasmic male sterility DNA factor can be discriminated by the presence or absence of the detected amplified genomic DNA. If necessary, more precise and exact discrimination becomes possible by detecting presence or absence of amplified genomic DNA by a method similar to that described above but changing the primer to be used.

In addition, more precise and exact discrimination can be made by optionally adjusting conditions of polyermase chain reaction such as the temperature of the annealing step for a primer, the concentration of magnesium in the buffer solution for reaction or the like.

The male sterility DNA factor of the present invention can also be utilized in the following method.

A method of discriminating a plant containing a cytoplasmic male sterility DNA factor as defined above, which comprises: conducting Southern or Northern hybridization on a genomic DNA or RNA of a plant as a sample for analysis using, as a probe, a cytoplasmic male sterility DNA factor as defined above or an equivalent thereof.

According to this method, it is readily determined as to whether or not the plant as the test specimen contains a cytoplasmic male sterility DNA factor.

The probe to be used in this method includes, a cytoplasmic male sterility DNA factor of SEQ ID NO: 1 or a part of it or a DNA containing said DNA or an equivalent of them.

The mitochondrial genomic DNA of a plant extracted from a tissue such as a flower, leaf, stem or the like or cultured cells of a plant as a test specimen by a conventional method as described above, or for example, an RNA of a plant collected from an RNA extract obtained by using guanidine thiocyanate/cesium chloride process followed by ethanol precipitation can be used.

This enables easy and short time discrimination of cytoplasmic male sterility and confirmation of fertility of a flower in a short period of time (the method of discrimination of hybridization of the present invention).

The term "Southern hybridization process" used herein will be explained below.

Southern hybridization process enables detection of a few pg of a DNA fragment which is complementary to a probe used with high sensitivity, and (1) it usually comprises:
digesting a DNA with an appropriate restriction enzyme to produce DNA fragments ranging from 100 bp to about 20 kbp,
fractionating the obtained DNA fragment by means of electrophoresis on agarose gel,
denaturing by an alkali to form a single stranded DNA,
neutralizing said single stranded DNA,
eluting with a high concentration salt solution making use of capillary phenomenon and simultaneously adsorbing onto a filter such as a nitrocellulose filter,
fixing the single stranded DNA by drying at an elevated temperature (80° C.), and
incubating said filter and the probe, for example, at about 40° C. to about 50° C. for about 10 hours to about 20 hours to cause hybridization;
alternatively (2) it comprises:

denaturing by heat at about 90° C. to about 100° C. for about 3 minutes to about 5 minutes to form a single stranded DNA, spotting said single stranded DNA on a nylon filter (Hybond N, trademark, manufactured by Amersham), drying on a filter paper, fixing the single stranded DNA by irradiating with ultraviolet rays, and incubating said filter and the probe, for example, at about 40° C. to bout 50° C. for about 10 hours to about 20 hours to cause hybridization. Conventional procedures for the hybridizations are described in Cloning and Sequence. Supervised by T. Watanabe, Edited by M. Sugiura, Published by Nosonbunkasya, 1989, and others.

Northern hybridization process enables detection of a few pg of an RNA fragment which is complementary to a probe used with high sensitivity, and (1) it usually comprises:

fractionating by means of electrophoresis on agarose gel (containing about 0.5M–about 2.2M formaldehyde) an RNA, for example, of about 100 bp to about 10 kbp, neutralizing said RNA, eluting with a high concentration salt solution making us of capillary phenomenon and simultaneously adsorbing onto a filter such as a nitrocellulose filter, fixing the RNA by drying at an elevated temperature (80° C.), and incubating said filter and the probe, for example, at about 40° C. to about 50° C. for about 10 hours to about 20 hours to cause hybridization; alternatively it usually comprises:

spotting said RNA on a nylon filter (Hybond N, trademark, manufactured by Amersham), drying on a filter paper, fixing the RNA by irradiating with ultraviolet rays, and incubating said filter and the probe, for example, at about 40° C. to about 50° C. for about 10 hours to about 20 hours to cause hybridization.

The probe used in the method of discrimination of the present invention is not particularly limited insofar as it is a DNA fragment or an oligonucleotide which hybridizes to a cytoplasmic male sterility DNA factor shown by SEQ ID NO: 1 or a part of it or a DNA containing said DNA or an equivalent of them and which is labelled beforehand with a radioisotope, an enzyme or the like, and may include a DNA fragment or an oligonucleotide having usually about 15 or more nucleotides.

Preferably, it includes a DNA fragment or an oligonucleotide having 30 or more nucleotides.

An example of the probe which can hybridize to a cytoplasmic male sterility DNA factor shown by SEQ ID NO: 1 is the total nucleotide sequence shown by SEQ ID NO:1.

An example of the probe which can hybridize to the cytoplasmic male sterility DNA factor which is a nucleotide sequence shown by SEQ ID NO: 1 or a part of it or a DNA containing the said DNA is a nucleotide sequence consisting of the nucleotide 1 to the nucleotide 150 in the nucleotide sequence shown by SEQ ID NO:1.

An example of the probe which can hybridize to an equivalent of a cytoplasmic male sterility DNA factor which is a nucleotide sequence shown by SEQ ID NO: 1 or a part of it or a DNA containing said DNA (for example, a RNA corresponding to a cytoplasmic male sterility DNA factor or a part of it or a DNA containing said DNA) is a nucleotide sequence lacking the nucleotide 61 to the nucleotide 78 in the nucleotide sequence shown by SEQ ID NO:1.

The expression "an equivalent of them (a cytoplasmic male sterility DNA factor which is a nucleotide sequence shown by SEQ ID NO: 1 or a part of it or a DNA containing said DNA)" means a cytoplasmic male sterility DNA factor having a nucleotide sequence of a cytoplasmic male sterility DNA factor which is a nucleotide sequence shown by SEQ ID NO: 1 in which a single nucleotide or plural nucleotides added, deleted or replaced (i.e., a DNA factor which is a part of a gene which can be specifically expressed in a male sterility cytoplasm and which has a function of providing male sterility as a result of, for example, ligation to a mitochondria gene) or an RNA corresponding to such DNA and refers to a nucleic acid polymer which is an analogue having the same function.

The oligonucleotide used as a probe in the method of discrimination of hybridization of the present invention can be obtained with a commerically available automatic DNA synthesizer using, for example, β-cyanoethyl phosphoramidite process or thiophosphite process. Also, it can be obtained by amplifying the whole length or a part of the nucleotide sequence shown by SEQ ID NO: 1 by PCR process using, as a template, a genomic DNA, plasmid or the like prepared from a male sterility strain having a cytoplasmic male sterility DNA factor which is a nucleotide sequence shown by SEQ ID NO: 1, or excising from a plasmid containing a cytoplasmic male sterility DNA factor which is a nucleotide sequence shown by SEQ ID NO: 1 with a restricting enzyme (for example, EcoRI, XbaI, BamHI, SalI or the like).

Labelling of the probe used in the method of discrimination of hybridization of the present invention can be carried out according to following methods:

a method of using a non-radioactive label such as one described in Prevention of Plant Epidemics. 44 (12), 549 (1990), or a method of using a usual radioactive label such as one described in The Newest Fundamental of Experiment in Agriculture, Edited by Department of Agriculture, Faculty of Agriculture, Tohoku University, Published by Softscience, Tokyo, 1990, "Protocol for Experiments in Plant PCR" Plant Cell Industry, Supplement, Supervised by Ko Shimamoto and Takuji Sasaki, Published by Shujunsha Co., Ltd., Tokyo, 1995, and the like.

Specifically, for example, the gene of the present invention or a part or an equivalent of them may be allowed to incorporate a radioactive nucleotide such as $[\alpha\text{-}^{32}P]dCTP$ or the like by nick translation method to produce a radioactive probe labelled with $^{32}P$ or the like, or allowed to incorporate a biotinylated nucleotide such as biotin-11-dUTP or biotin-14-dATP by nick translation method or random priming method to produce a labelled non-radioactive probe, or allowed to bridging an enzyme such as alkaline phosphatase, perioxidase or the like to a nucleotide site with glutaraldehyde to produce a labelled non-radioactive probe.

When a radioactive probe labelled with $^{32}P$ or the like is used as the probe, a signal is detected by exposing to an X-ray film without further treating.

When a non-radioactive probe labelled with a biotinylated nucleotide is used, a signal is detected by labelling with biotinylated alkaline phosphatase with the intermediation of streptavidin, combining with nitroblue-tetrazonium and 5-bromo-4-chloro-3-indolyl phosphate as substrates and observing color development due to the substrate or exposing the radiation to an X-ray film.

When a non-radioactive probe labelled with an enzyme such as alkaline phosphatase, peroxidase or the like is used, a signal is detected by using 4-methoxy-4-(3-phosphatophenyl)spiro[1,2-dioxyethane-3,2-adamantane] (PPD) or the like in the former case or luminol or the like in the latter case and observing color development due to the substrate or exposing the radiation to an X-ray film.

The male sterility DNA factor of the present invention can further be utilized in the following manner:

By culturing the microorganism of the present invention, i.e., the microorganism holding the plasmid containing the cytoplasmic male sterility DNA factor according to the conventional manner, a protein corresponding to said cytoplasmic male sterility DNA factor is produced.

The protein is recovered from the microorganism, purified and an antibody to said protein is produced in the conventional manner using the purified protein. By carrying out Western blotting method on a protein sample for analysis extracted from a plant using the produced protein, a plant containing the cytoplasmic male sterility DNA factor can be discriminated.

Also, by ligating the sterility DNA factor of the present invention, for example, to downstream of a cytoplasmic fertility type mitochondria gene (removing the termination codon of the cytoplasmic fertility type mitochondria gene and matching frames), a cytoplasmic male sterility type mitochondria gene, i.e., the sterility type gene of the present invention, can be constructed. The gene constructed in this manner is useful in controlling fertility of a plant, and further, by cloning said gene using, for example, a commercially available plasmid vector (for example, pCRII, manufactured by Invitrogen) and a method described in a kit, a plasmid containing said cytoplasmic male sterility type mitochondria gene and a microorganism holding such plasmid can be obtained.

Figure 2:
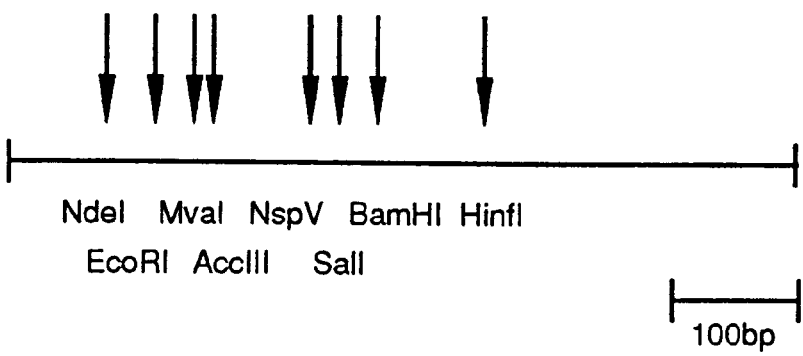
FIG. 2 shows restriction map representing the structure of a cytoplasmic male sterility type mitochondria gene (structural gene region) of the present invention, wherein restriction sites, NdeI (80 bp), EcoRI (117 bp), MvaI (152 bp), AccIII (165 bp), NspV (249 bp), SalI (275 bp), BamHI (300 bp) and HinfI (485 bp) are indicated by arrows.

Next, a description will be made to a DNA comprising a nucleotide sequence selected from the group consisting of:

(a) a nucleotide of 651 bp and having a restrictions map as depicted in FIG. 2 and has restriction sites, NdeI (80 bp), EcorI (117 bp), MvaI (152 bp), AccIII (165 bp), NspV (249 bp), SalI (275 bp), BamHI (300 bp) and HinfI (485 bp), (b) a nucleotide sequence shown by SEQ ID NO: 3;

(c) a nucleotide sequence encoding the amino acid sequence depicted in SEQ ID NO:4; and a nucleotide sequence hybridizing with a nucleotide sequence of (b) or (c).

The said DNA is a sterility type gene and can be obtained, from a DNA extracted from a tissue or cultured cells of a plant such as carrot or the like by a similar manner as described above and by using the following oligonucleotide primers:

5' ATGCCTCAACTGGATAAATT 3' (SEQ ID NO:15) and
5' CTATTTTGAATTTTTTTCCGT 3' (SEQ ID NO:12).

The DNA fragment of 651 bp obtained in this manner is identified by a restriction map shown in FIG. 2 and its precise structure can be represented by a nucleotide sequence shown by SEQ ID NO: 3.

The DNA fragment can be cloned by a method described in a kit with a commercially available plasmid vector (for example, pCRII manufactured by Invitrogen) to obtain a plasmid containing said cytoplasmic male sterility type mitochondria gene and a microorganism carrying said plasmid.

For transforming a plant cell or a plant by introducing the sterility type mitochondria gene of the present invention, and (expression) plasmid in which the sterility type mitochondria gene of the present invention is ligated downstream of a cauliflower mosaic virus 35S promotor, or an (expression) plasmid in which F1-ATPase β subunit gene mitochondrial signal presequence (described in EMBO J, 4, 2159–2165 (1985), Plant Mol. Biol., 24, 631–641 (1994)).

The sterility type mitochondria gene of the present invention which is ligated downstream of a cauliflower mosaic virus 35S promotor is introduced by any of conventional means such as Agrobacterium infection method (JP-B-2-58917 and JP-A-60-70080), electroporation method into protoplast (JP-A-60-251887 and JP-A-5-68575), particle gun method (JP-A-508316 and (JP-A-63-258525) and the like.

The plant cell into which the sterility type mitochondria gene of the present invention is introduced is selected and a plant is regenerated by a conventional plant cell culturing process, for example, described in Utimiya, Manual for Plant Gene Manipulation (Method for Producing Transgenic Plants), Published by Kodansha Scientific, 1990, pages 27–55, to obtain a transformed plant.

EXAMPLES

The present invention will now be described in more detail by means of Examples. These examples should not be construed as a limitation upon the scope of the present invention but various alterations will no doubt become possible by usual modification in the art of this invention.

Example 1 (Isolation of a mitochondrial genomic DNA derived from carrot)

Following carrot (*Daucus carota* L.) Strains and cultivars were used. Cytoplasmic fertility pure line cultivars, trade name: "Nagafutorikintoki", trade name: "Kokubusenkoudicho", trade name: "Imperator", trade name: "Koizumirisogosun", trade name: "Nantes Scarlet", trade name: "Kikuyougosun" and existing generations and progenies of other commercially available cultivars were grown and flowered. Cytoplasmic male sterility strains MS-1 and MS-2, for which it was confirmed that all the flowers exhibited male sterility and that the character was cytoplasmic, were used as the materials and mitochondrial DNA was isolated from each of them by the following method.

Lower hypocotyls of non-symbiotically germinated carrot strains and cultivars described above at 10 days age were sterilized with Antiformin having an available chlorine concentration of 1% for 20 minutes, sufficiently washed with sterilized water, placed on a solid medium prepared by solidifying MS medium, supplied with 1 mg/l 2,4-D (2,4-dichlorophenoxyacetic acid), by 0.8% agar powder, cultivated at 25° C. to form callus. After about 1 month of cultivation, callus was finely divided, placed on a solid medium prepared by solidifying MS medium, supplied with 0.5 mg/l 2,4-D, by 0.8% agar powder, and subcultured about every 1 month. The cali were finely divided again, transferred to a liquid medium prepared by adding 0.5 mg/l 2,4-D to MS medium and cultivated with shaking at 100 rpm at 25° C. for about 3 weeks. Thereafter, about ½₀ amount each was subcultured in a fresh medium once in two-week and liquid subculture cells were established. About 10 g of the liquid subculture cells after subcloning for three days were collected by centrifugation and treated in a enzyme solution (pH 5.7) containing 0.5% Cellulase Onozuka RS, 1% Driselase, 0.01% Pectolyase Y-23, 0.1% MES (2-(N-morpholino)ethanesulfonic acid) and 0.5M Mannitol with gentle shaking at 50 rpm at 30° C. in the dark to obtain crude protoplast solutions. The crude protoplast solutions were filtered through a stainless steal mesh having a pore size of 32 µm to remove cell wall debris. The obtained protoplasts were gently suspended in a washing solution of 0.5M Mannitol (pH 5.7), centrifuged at 150 g for 3 minutes, combined with the washing solution and gently stirred to suspend the protoplasts. The same procedure was repeated twice to give purified protoplasts.

The purified protoplasts were suspended in 0.4M sorbitol solution containing 40 ml of 100 mM Tris-HCl, 1 mM EDTA, 1% (wt/v) BSA and 0.3% (wt/v) 2-mercaptoethanol and incubated on ice for 20 minutes. The protoplasts were pricked several times with a 18 gauge needle to gently destruct protoplast membrane, Membrane-destructed protoplasts suspension was centrifuged (3,000 g, 10 minutes) to precipitate nuclei. The supernatant was centrifuged (6,000 g, 5 minutes) to precipitate a mixed fraction of nuclei and plastids. The supernatant was taken, the above described procedure was once repeated. The supernatant was separated again and then centrifuged (15,000 g, 15 minutes) to collect precipitate (a mitochondrion fraction). The obtained precipitate was gently treated with 50 mM Tris-HCl buffer (pH 7.5) containing DNase, 10 mM $MgCl_2$ and 0.3M sucrose for 30 minutes. In order to remove DNase, the mitochondria solution was layered over 10 mM Tris-HCl buffer (pH 7.2) containing 0.02M EDTA and 0.6M sucrose and centrifuged (15,000 g, 10 minutes). The obtained precipitate was treated with 50 mM Tris-HCl buffer (pH 8.0) containing 100 µg of Proteinase K, 1% (wt/v) N-lauryl sarcosine and 20 mM EDTA at 37° C. for 1 hour to digest mitochondrial membrane. To this was added equal amount of phenol and chloroform-isoamyl alcohol (chloroform/isoayml alcohol=24/1) and they were mixed with shaking for 15 minutes. The mixture was centrifuged (1,940 g, 15 minutes). The obtained aqueous layer was separated, again combined with equal amount of phenol and chloroform-isoamyl alcohol (chloroform/isoamyl alcohol=24/1) and they were mixed with shaking for 15 minutes. The mixture was centrifuged (1,940 g, 15 minutes). The obtained aqueous layer was separated, combined with 2.5 times the amount of ethanol and they are mixed with several times of shaking. After centrifugation (1,940 g 10 minutes), the precipitate was separated and washed with 70% ethanol. The precipitate obtained upon centrifugation (1,940 g, 15 minutes) was dried under reduced pressure. The precipitate was suspended in 50 mM Tris-HCl buffer (pH 7.5) containing 0.4 ml of 1 mM EDTA. After whole precipitate was completely dissolved, 2.5 units of RNase (manufactured by Wako Pure Chemical Industries, Ltd.) was added to the solution, which was then incubated at 37° C. for 1 hour.

To the obtained solution was added equal amount of phenol and chloroform-isoamyl alcohol (chloroform/isoamyl alcohol=24/1) and they were mixed with shaking for 15 minutes. The mixture was centrifuged at 1,940 g for 15 minutes. The obtained aqueous layer was separated, again combined with equal amount of phenol and chloroform-isoamyl alcohol (chloroform/isoamyl alcohol=24/1) and they were mixed with shaking for 15 minutes. The mixture was centrifuged at 1,940 g for 15 minutes. The obtained aqueous layer was separated, combined with 2.5 times the amount of ethanol and they are mixed with several times of shaking. After centrifugation at 1,940 g for 10 minutes, the precipitate was separated and washed with 70% ethanol. The precipitate obtained upon centrifugation at 1,940 g for 15 minutes was dried under reduced pressure. The precipitate was suspended in 50 mM Tris-HCl buffer (pH 7.5) containing 0.4 ml of 1 mM EDTA. In this manner, about 5–10 µg of mitochondrial genomic DNA was obtained.

Example 2 (Search for the sterility DNA factor of the present invention by RAPD method)

Polymerase chain reaction was carried out in 10 mM Tris-HCl buffer (pH 8.3) containing 0.01% (wt/v) gelatin, to which 20 pmol of 10 kinds of 10 mer RAPD primers OPB 1–10 (manufactured by Operon), 2.5 unit heat resistant DNA polymerase (manufactured by Takara Shuzo), 1.0 nmol of each of 4 kinds of nucleotides (dATP, dTTP, dCTP and dGTP) and 0.2 µg of each of mitochondrial genomic DNAs from carrot strains and cultivars obtained in Example 1 were added, and 50 mM magnesium chloride. The amount of the reaction solution was 20 µl and about 20 µl of mineral oil was added in order to prevent evaporation. The polymerase chain reaction was carried out by the following conditions.

The first cycle comprising the denaturation step at 94° C. for 5 minutes, the annealing step for the primer by incubating with a primer at 40° C. for 2 minutes and the elongation step with heat resistant DNA polymerase at 72° C. for 3 minutes was carried out once. Then, the second cycle comprising the denaturation step at 94° C. for 1 minute, the annealing step for the primer at 40° C. for 2 minutes and the elongation step with DNA polymerase for 40 seconds at 72° C. for 3 minutes 40 times. Further, the third cycle comprising the denaturation step at 94° C. for 1 minute, the annealing step for the primer at 40° C. for 2 minutes and the elongation step with DNA polymerase at 72° C. for 10 minutes was carried out once.

The amplified mitochondrial DNA was separated by electrophoresis in 40 mM Tris-20 mM acetate buffer (pH 8.0) containing 1 mM EDTA at 100 V for 35 minutes using 1.5% agarose gel. As size markers, 100 nucleotide marker and kilo nucleotide marker (manufactured by Pharmacia) were used. After separation, the gel was immersed in 0.5 µg/ml aqueous ethidium bromide solution for 30 minutes and irradiated with ultraviolet rays at 254 nm in the dark to detect red bands by the complex of DNA and ethidium bromide. As a result, when OPB 04 (5' GGACTGGA 3'; Operon) was used, a band of about 1.1 kb was detected only for all the cytoplasmic male sterility strains. The bands of 1.1 kb were excised from the gel, purified, integrated into pCRII vector according to a protocol of TA Cloning Kit (manufactured by Invitogen), used to transform *E. coli* and amplified. Then, the plasmid was purified and about 300 bps at both ends in the DNA fragment of about 1.1 kb were sequenced by ABI 373S-18 DNA Sequencer. Investigation of homology indicated that 3' end of the DNA fragments of about 1.1 kb had a very high homology with about 200 bp from the initiation codon in mitochondrial orf B gene of sunflower.

Example 3 (Search for the sterility DNA factor of the present invention by PCR method)

In order to reconfirm that the DNA fragments of about 1.1 kb were a specific DNA (containing cytoplasmic male sterility DNA factor) detected only in the cytoplasmic male sterility strains, PCR process was conducted, using, as templates, mitochondrial genomic DNAs isolated from cytoplasmic fertility pure line cultivars of carrot such as "Kokubusenkoudaicho" and "Imperator", and cytoplasmic male sterility strains 493S, 2566A and 9304A in the same manner as in Example 1 and, as primers, oligonucleotides et on the basis of the nucleotide sequence in orf B gene of sunflower under the following conditions.

The polymerase chain reaction was carried out in 10mM Tris-HCl buffer (pH 8.3) containing 0.01% (wt/v) gelatin, to which 20 pmol of oligonucleotides shown by the nucleotide sequences:
(1) 5' ATGCCTCAACTGGATAAATT 3' (SEQ ID NO:15)
(2) 5' TTAAAAACCGATGCTTCCTT 3' (SEQ ID NO:16)
which were the oligonucleotides set on the basis of the nucleotide sequence in orf B gene of sunflower, 2.5 unit heat resistant DNA polymerase (manufactured by Takara Shuzo), 1.0 nmol of each of 4 kinds of nucleotides (dATP, dTTP, dCTP and dGTP) and 20 ng of each of mitochondrial genomic DNAs from carrot strains and cultivars described above were added, 50 nM potassium chloride and 2 mM magnesium chloride. The amount of the reaction solution was 20 μl and about 20 μl of mineral oil was added in order to prevent evaporation. The polymerase chain reaction was conducted by the following conditions.

The first cycle comprising denaturation step at 94° C. for 5 minutes, the annealing step for the primer at 55° C. for 2 minutes and the elongation step with DNA polymerase at 72° C. for 3 minutes was carried out once. Then, the second cycle comprising the denaturation step at 94° C. for 1 minute, the annealing step for primer at 55° C. for 1 minute and the elongation step with DNA polymerase at 72° C. for 3 minutes was carried out 30 times. Further, the third cycle comprising the denaturation step at 94° C. for 1 minute, the annealing step for the primer at 55° C. for 1 minute and the elongation step with DNA polymerase at 72° C. for 10 minutes was carried out once.

The amplified genomic DNA was separated by electrophoresis in 40 mM Tris-20 mM acetate buffer (pH 8.0) containing 1 mM EDTA at 100 V for 35 minutes using 1.5% agarose gel. As size markers, 100 nucleotide marker and kilo nucleotide marker manufactured by Pharmacia were used. After separation, the gel was immersed in 0.5 μg/ml aqueous ethidium bromide solution for 30 minutes and irradiated with ultraviolet rays at 254 nm in the dark to detect red bands by the complex of DNA and ethidium bromide.

As a result, it was found that DNA fragments of about 1.2 kb were amplified for cytoplasmic male sterility strains 493S, 2566A and 9304A. On the other hand, DNA fragments of about 480 bp were amplified for cytoplasmic fertility pure line cultivars "Kokubusenkoudaicho" and "Imperator". From these results, it was reconfirmed that the amplified DNA fragments of about 1.2 kb were DNA (containing cytoplasmic male sterility DNA factor) specific only for the cytoplasmic male sterility strains.

Example 4 (Identification of sterility DNA factor of the present invention)

The DNA fragment of about 1.2 kb obtained from the cytoplasmic male sterility strain 493S and the DNA fragment of about 480 bp obtained from cytoplasmic fertility pure line cultivar "Imperator" were excised from the gel and the amplified DNAs were purified using DNA Purification Kit (manufactured by Bio Rad). They were integrated into pCRII vector using TA Cloning Kit (manufactured by Invitogen) according to a protocol described in the kit, transformed using INV αF' One Shot Kit (manufactured by Invitrogen) and selected according to a method described in the kit. The obtained positive clones were grown in LB liquid medium containing 100 mg/l Ampicillin and plasmids were purified using Flexiprep (manufactured by Pharmacia). Using M13 and M13 reverse primers and with ABI Prism Dye Terminator Cycle Sequencing Ready Reaction Kit (manufactured by Perkin-Elmer), 0.3 αg of the obtained plasmids were amplified and ethanol-precipitated, amplified DNAS were sequenced using 373A Sequencer (manufactured by ABI). As a result, the following nucleotide sequences were obtained:

(1) A nucleotide sequence of the DNA fragment of about 1.2 kb obtained form the cytoplasmic male sterility strain 493S: 1193 bp (SEQ ID NO:7) encoding the amino acid sequence depicted in SEQ ID NO:8.
2) A nucleotide sequence of the DNA fragment of about 480 bp obtained from the cytoplasmic fertility pure line cultivar "Imperator": 480 bp (SEQ ID NO:5) encoding the amino acid sequence depicted in SEQ ID NO:6.

In the nucleotide sequence of the DNA fragment of about 1.2 kb obtained from the cytoplasmic male sterility strain 493S, a initiation codon ATG (No. 1 to No. 3 nucleotides in SEQ ID NO:7) and a termination codon TAG (No. 649 to No. 651 nucleotides in SEQ ID NO:7) were found and it was confirmed that a 651 bp cytoplasmic sterility type mitochondria gene (structural gene region) was present. Similarly, in the nucleotide sequence of the DNA fragment of about 480 bp obtained from the cytoplasmic fertility pure line cultivar "Imperator", a initiation codon ATG (No. 1 to No. 3 nucleotides in SEQ ID NO: 5) and a termination codon TAG (No. 478 to No. 480 nucleotides in SEQ ID NO: 5) were found and it was confirmed that a 480 bp cytoplasmic fertility type mitochondria gene (structural gene region) was present. When structures of the former cytoplasmic sterility type mitochondria gene and the cytoplasmic fertility type mitochondria gene were compared, it was found that a No. 1 to No. 480 nucleotide region in each of the both nucleotide sequence had a high homology, and as a result, it was revealed that a No. 481 to No. 651 nucleotide region (171 bp) in the latter cytoplasmic fertility type mitochondria gene was the cytoplasmic male sterility DNA factor.

Example 5 (Discrimination of a plant having a cytoplasmic male sterility DNA factor by the method of discrimination of the present invention; part 1)

A PCR reaction was conducted using, as primers, a combination of oligonucleotides:
(1) 5' ATGCCTCAACTGGATAAATT 3' (SEQ ID NO:15)
(5) 5' CTATTTTGAATTTTTTTCCG 3' (SEQ ID NO:17)
which can amplify a DNA containing the nucleotide sequence shown by SEQ ID NO: 1, the cytoplasmic male sterility DNA factor, and using, as template, 100 ng of genomic DNAs isolated from cytoplasmic fertility pure line cultivars strains of carrot "Kokubusenkoudaicho", "Imperator", 493N, 2566B and 9304B, or cytoplasmic male sterility strains 493S, 2566A and 9304A with Isoplant (manufactured by Wako Fine Chemical Industries, Ltd.) in a manner similar to that in Example 3, specific genomic DNA (a part of sterility DNA factor of the present invention) was amplified, and after separating said amplified genomic DNA by electrophoresis, the amplified genomic DNA was visually detected. As a result, a DNA fragment of 651 bp was amplified and detected and hence the presence of the sterility DNA factor of the present invention was confirmed only for the cytoplasmic male sterility strains.

Example 6 (Discrimination of a plant having a cytoplasmic male sterility DNA factor by the method of discrimination of the present invention; part 2)

By conducting PCR reaction using, as primers, a combination of oligonucleotides:
(1) 5' ATAACGCTAATCCATGTTCCA 3' (SEQ ID NO:18)
(5) 5' GCTTGCAATATTCGATATAG 3' (SEQ ID NO:19)
which can amplify a DNA containing the nucleotide sequence shown by SEQ ID NO: 1, the cytoplasmic male sterility DNA factor, or a part or a DNA containing said DNA and using, as templates, 100 ng of genomic DNAs isolated from 493N, 2566B and 9304B as cytoplasmic fertility pure line cultivars or strains of carrot and 493S, 2566A and 9304A as cytoplasmic male sterility strains with Isoplant (manufactured by Wako Fine Chemical Industries, Ltd.) in a manner similar to that in Example 3, specific genomic DNA (a part of sterility DNA factor of the present invention) was amplified, and after separating said amplified genomic DNA by electrophoresis, the amplified genomic DNA was visually detected. As the result, a DNA fragment of about 250 bp was amplified and detected and hence the presence of the sterility DNA factor of the present invention was confirmed only in the cytoplasmic male sterility strains. On the other hand, in the cytoplasmic male sterility strains. On the other hand, in the cytoplasmic fertility pure line strains, a DNA fragment of about 280 bp was amplified and detected. Further, in the cytoplasmic male fertility strain 9304A, both of the DNA fragment of about 250 bp and the DNA fragment of about 280 bp were amplified and detected, indicating that the sterility DNA factor of the present invention acted dominantly.

Example 7 (Discrimination of a plant having a cytoplasmic male sterility DNA factor by the method of discrimination of hybridization of the present invention; part 1)

1. Preparation of a probe

Using mitochondrial genomic DNA of 493S obtained in Example 3 as a template and primers (primers: 5' TAT-GACTCCTTCTTTCACTT 3' (SEQ ID NO:9), 5' CTATTTTGAATTTTTTTCCG 3' (SEQ ID NO:17) designed such that a No. 481 to No. 651 nucleotide region in the nucleotide sequence shown by SEQ ID NO:3 as primers, PCR reaction was conducted in a manner similar to that in Example 3. The obtained DNA fragment was dissolved in distilled water adjusting to 100 ng/10 μl and DNA was denatured by heating at 100° C. for 5 minutes. Immediately after the denaturation, the solution was left to stand in ice water for 5 minutes to give single stranded DNA. Said DNA was converted to a non-radioactive probe having a peroxidase cross-linked to a nucleotide site as a label using a commercially available ECL Direct Nucleic Acid Labelling System (manufactured by Amersham).

2. Preparation of a membrane

Using 10 units of a restriction enzyme BamHI (manufactured by Takara Shuzo), 0.5 μg of mitochondrial DNAs obtained from cytoplasmic male sterility strains of "MA-1" and "MS-2" and five commercial fertility cultivars, "Kokubusenkoudaicho", "Imperator", "Nagafutorikintoki", "Koizumirisougosun" and "Kikugougosun" is Example 1 were digested under conditions recommended by the maker and the product was electrophoresed in 0.8% agarose gel at 40 V for 16 hours to separate mitochondrial DNAs. The gel containing separated DNAs was shaken in 0.25M HCl for 10 minutes, gently washed with distilled water, placed on a platform for blotting and transferred to Hybond-N+ (manufactured by Amersham) membrane with 0.4N NaOH for 4 hours. In order to fix the adhered DNAs, the dried membrane was heated at 80° C. for 2 hours.

3. Hybridization

Figure 3:
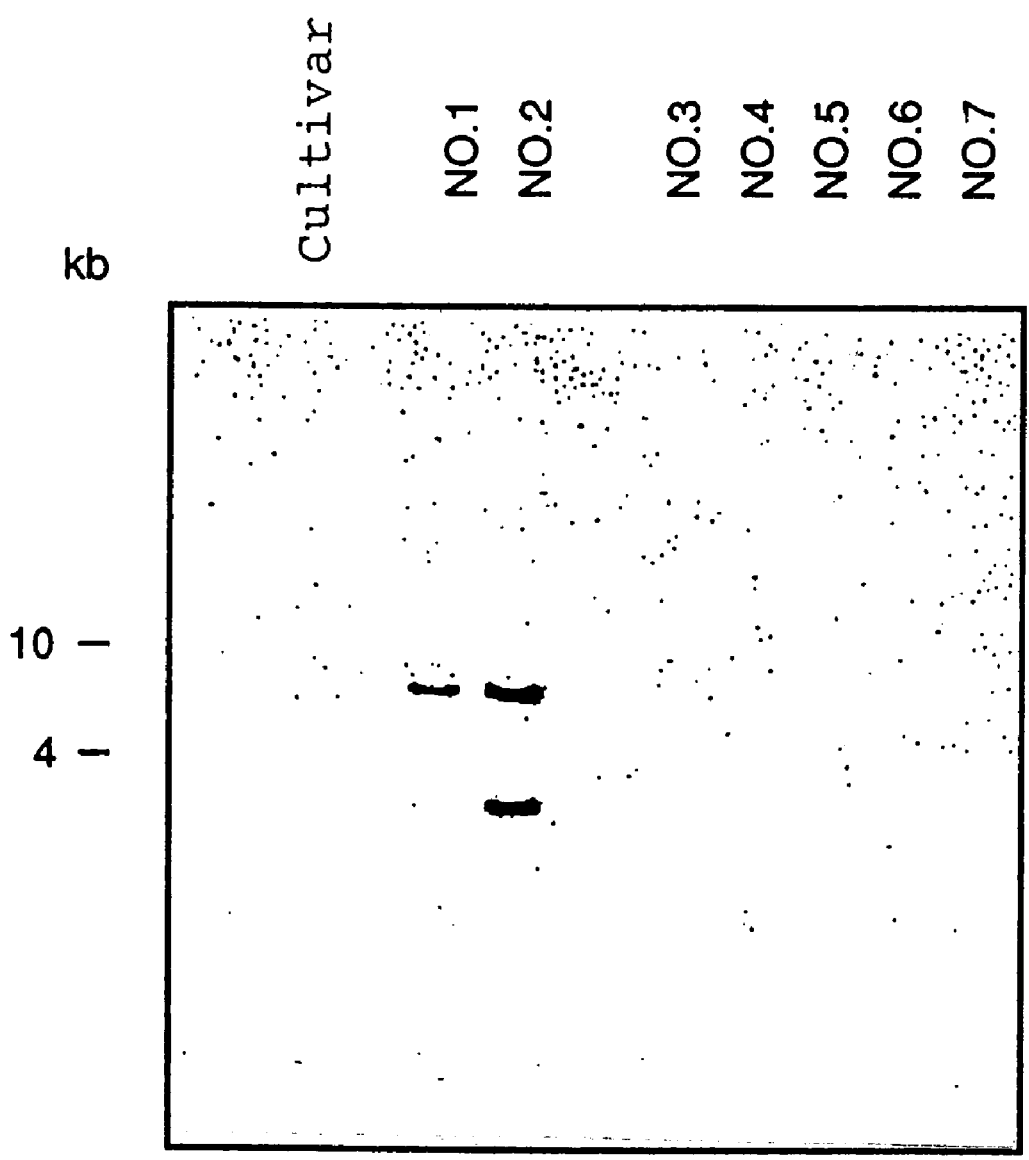
FIG. 3 shows results of detecting signals in the method of discrimination of hybridization of the present invention.

Using ECL Detection Kit (manufactured by Amersham), 4 cm$^2$ of the DNA-fixed membrane prepared in 2 and 1 ml of a hybridization buffer containing 0.5M sodium chloride per 4 cm$^2$ of the DNA-fixed membrane prepared in 2 was charged in a hybripack, which was heat-sealed, and hybridization was carried out at 42° C. for 20 minutes. Then, the probe prepared in 1 was added in the hybripack and the mixture was incubated with gentle shaking at 42° C. for 12 hours to form DNA—DNA hybrids. After reaction, said DNA-fixed membrane was twice washed with 2×SSC (7.5 mM sodium citrate, 75 mM sodium chloride, pH 7.0) containing 6M urea and 0.1% SDS per 1 cm$^2$ of said membrane. Then, it was twice washed in 0.1×SSC at room temperature for 5 minutes. Thereafter, it was immersed in a detection reagent mixture (ECL Direct Labelling System (manufactured by Amersham) at room temperature for 1 minute to cause luminescence reaction of the probe. An X-ray film was exposed to the luminescence and developed and a positive hydridized band was detected only in cytoplasmic male sterility strains MS-1 and MS-2 (see FIG. 3).

Example 8 (Discrimination of a plant having a cytoplasmic male sterility DNA factor by the method of discrimination of hybridization of the present invention; part 2)

1. Preparation of a probe

According to a method of Megalabel Kit (manufactured by Takara Shuzo), 100 ng of the cytoplasmic male sterility DNA factor of the cytoplasmic male sterility strain 493S obtainable in a manner similar to that in 1 of Example 7 is labelled with γ-$^{32}$PdATP (1.85 MBq, 50 μCi) at 5' end of the DNA. Briefly, after dephosphorylating 100 ng of the template DNA, it is extracted with phenol and precipitated by ethanol to give dehosphorylated DNA. To a solution of the obtained dephosphorylated DNA in 20.5 μl are added 2.5 μl of 10×buffer (Megalabel Kit (manufactured by Takara Shuzo)), 1 μl of γ-$^{32}$PdATP (1.85 MBq, 50 μCi) and 1 μl of T4 Polynucleotide Kinas (10 U/μl) and the mixture is incubated at 37° C. for 30 minutes. Then, it is heated at 70° C. for 5 minutes to inactivate the enzyme and precipitated by ethanol. The formed precipitates are dissolved in an appropriate buffer and combined with 1 mg of salmon sperm DNA. The mixture is heated at 95° C. for 5 minutes, cooled in ice and used as a probe.

2. Extraction of whole RNA

Each 100 mg of leaf and flower from the cytoplasmic male sterility strains "2566A" and "9304A" as well as the fertility strains "2566B", "9304B" and "Imperator" is triturated in liquid nitrogen, combined with 1 ml of Isogen (manufactured by Wako Pure Chemical Industries, Ltd.) and the mixture is left to stand at room temperature for 10 minutes. To said mixture is added 200 μl of chloroform/isoamyl alcohol (24/1). The mixture is sufficiently stirred and centrifuged. The aqueous layer is transferred to another vessel and combined with 500 μl of isopropyl alcohol. The mixture is left to stand for 5 minutes and centrifuged to obtain a precipitate. After washing the obtained precipitate with 70% ethanol, the precipitate is collected by centrifugation, dried up and dissolved in 200 μl of TE buffer to give the whole RNA.

3. Electrophoresis and transfer to a membrane

A mixture of a solution of 20 μg of the extracted whole RNA in 5 μl of distilled water and 16 μl of loading Buffer [a mixed solution of 1.6 ml formaldehyde (37%), 5.0 ml formamide, 0.5 ml 20×MOPS and 1.6 ml glycerol dye solution (50% glycerol, 0.1 mg/ml bromophenolblue, 0.1 mg/ml xylenecyanol and 1 mM EDTA)] added thereto is incubated at 65° C. for 10 minutes and then electrophoresed in denatured agarose gel (1.17% agarose, 0.66M formaldehyde, 1×MOPS (3-(N-morpholino)propane sulfonic acid) at 110 V for 2 hours. Said gel is placed on a platform for transferring and transferred to Hybond-N (manufactured by Amersham) membrane with 20×SSC for 12 hours. The membrane to which RNA is blotted is gently washed with 2×SSC, air-dried and irradiated with ultraviolet rays on a transilluminator for 5 minutes to fix the RNA on the membrane.

4. Detection

Into a hybripack is placed 0.033 ml/cm$^3$ membrane area of QuikHyb solution (manufactured by Strategene) and hybridization is carried out with the membrane at 50E for 15 minutes. After adding the probe labelled in 1 and heat-sealing the hybripack, hybridization is carried out at 50° C. for 1 hour. Then, it is twice washed with shaking in 2×SSC containing 0.1% SDS at room temperature for 15 minutes and further washed in 0.1% SSC containing 0.1% SDS at 50° C. for 30 minutes. An imaging plate (manufactured by Fuji Film) is exposed to membrane for 12 hours and RI is detected using BAS 2,000 (manufactured by Fuji Film). As the result, about 800 bp transcription product is found only in "2566A" and "9304A". By the presence or absence of the transcription product, male sterility cytoplasm (2566A and 9304A) can be discriminated.

Example 9 (Construction of (sterility type) plasmid of the present invention)

In order to construct a plasmid characterized by containment of the sterility DNA factor of the present invention (see FIG. 4), primers are prepared having sites for restriction enzymes XbaI and ScaI (manufactured by Takara Shuzo) connected to 5' ends of two nucleotides:
(1) 5' ATGCCTCAACTGGATAAATT 3' (SEQ ID NO:15)
(2) 5' CTATTTTGAATTTTTTTCCG 3' (SEQ ID NO:17)
which can amplify a DNA containing the nucleotide sequence shown by SEQ ID NO: 1, the cytoplasmic male sterility DNA factor, and using this and a mitochondrial genomic DNA isolated in a manner similar to that in Example 1 as a template, PCR process is conducted in a manner similar to that in Example 3 to amplify the sterility DNA factor of the present invention. The amplified PCR product is digested with both restriction enzyme and the desired product is collected.

On the other hand, GUS expression binary vector pBI121 (manufactured by Clontech) derived from pBIN is digested by restriction enzymes XbaI and SacI and fragments lacking GUS structural gene are collected.

Both products are ligated with T4 DNA ligase (DNA ligation kit, manufactured by Takara Shuzo) and the product is used to transform the competent cell of *E. coli* HB 101 strain (manufactured by Toyobo). Ampicillin resistant strains are selected. As another option, it is more preferred to ligate, for example, a coding region for a transit peptide in a gene which is encoded in a nucleic DNA such as ATPase b subunit gene of a higher plant and which has a transport signal to a mitochondrion called transit peptide at an amino acid terminal of a translated protein between 35S promoter in pBI121 vector derived from cauliflower mosaic virus and the sterility DNA factor of the present invention. Further, among plasmids grown from Ampicillin resistant strains, clones in which the sterility DNA factor of the present invention is inserted in the normal or reverse orientation in relation to the terminator derived from nopaline synthase in the 35S promoter derived from cauliflower mosaic virus to obtain a (sterility type) plasmid pDCMS-1 of the present invention.

Furthermore, the (sterility type) plasmid pDCMS-1 of the present invention is transferred to *Agrobacterium tumefaciens* LLBA4404 by electroporation method and stored.

Example 10 (Production of (sterility type) plant of the present invention; part 1)

Into a culture solution obtained by culturing overnight the (sterility type) microorganism of the present invention produced in Example 9 is immersed 0.5–1 cm of lower hypocotypls of cytoplasmic fertility type carrot non-symbiotically germinated and cultured for 1 week in a manner similar to that in Example 1. The lower hypocotyls of cytoplasmic fertility type carrot infected by the (sterility type) microorganism of the present invention is cultured in MS medium containing 3% saccharose and 4.5 μM 2,4-D under conditions of 22° C. in the light for 2–3 days. After cultivation, it is washed with the above MS medium containing 500 mg/l Cefotaxime and cultured for 4 weeks appropriately subculturing in MS medium containing 3% saccharose, 0.8% agar powder, 4.5 μM 2,4-D and 300 mg/l Cefotaxime, Then, it is cultured for 8 weeks appropriately subculturing in MS medium containing 3% saccharose, 0.8% agar powder, 4.5 μM 2,4-D, 200 mg/l Cefotaxime and 50 mg/l Kanamycin under conditions of 22° C. and 16 hours light/8 hours dark. After primary selection, it is cultured in MS medium containing 3% saccharose and 0.8% agar powder allowing to form adventitious buds. Thereafter, secondary selection is conducted by culturing in MS medium containing 3% saccharose, 0.8% agar powder and 50–100 mg/l kanamycin and the obtained seedlings are acclimatized to obtain transformed carrots which are (sterility type) plant bodies of the present invention.

In a similar manner, the (sterility type) microorganism of the present invention obtained in Example 9 is infected to non-symbiotically cultured tobacco leaf according to a method described in Uchimiya, Manual for Plant Gene Manupulation, Published by Kodansha Scientific, 1990, pages 27–33, to obtain transformed tobacco cells and a plant therefrom.

Example 11 (Production of (sterility type) plant of the present invention; part 2)

The (sterility type) plasmid of the present invention obtained in Example 9is introduced into an adventitious bud of soybean with a particle gun according to a method described in JP-A-3-291501 to obtain transformed soybean cells and a plant therefrom. Similarly, it is introduced into an unripe scutellum of rice with a particle sun according to a method described in Shimade et al., Ikushugaku Zasshi (1994), 44, Supplement 1, 66, to obtain transformed rice cells and a plant therefrom. Similarly, it is introduced into an unripe scutellum of wheat with a particle gun according to a method Supplement 1, 57, to obtain transformed wheat cells and a plant therefrom. Similarly, it is introduced into an adventitious bud of maize with a particle gun according to a method described in M. E. Fromm et al., Bio Technology, 1990, 8, 833–839, to obtain transformed maize cells and a plant therefrom.

We claim:

1. An isolated cytoplasmic male sterility mitochondria gene, comprising a nucleotide sequence selected from the group consisting of:
   (a) a nucleotide sequence shown by SEQ ID NO:1,
   (b) a nucleotide sequence encoding the amino acid sequence depicted in SEQ ID NO:2, and
   (c) a nucleotide sequence comprising a nucleotide sequence of 171 bp having a restriction map shown by FIG. 1 and having restriction sites, HinfI (5 bp), MboI (24 bp), MboI (43 bp) and HapII (122 bp)nucleotide sequence of 171 bp, and hybridizing under conditions wherein single stranded DNA having the nucleotide sequence of (c) is fixed on a filter and then the filter is incubated with a probe having the nucleotide sequence of (a) or (b) at about 40° C. to about 50° C. for about 10 hours to about 20 hours to cause hybridization.

2. An isolated cytoplasmic male sterility mitochondria gene, comprising a nucleotide sequence selected from the group consisting of:
   (a) a nucleotide sequence shown by SEQ ID:3,
   (b) a nucleotide sequence encoding the amino acid sequence depicted in SEQ ID NO:4, and
   (c) a nucleotide sequence comprising a nucleotide sequence of 651 bp having a restriction map as depicted in FIG. 2, and having restriction sites, Nde1 (80 bp), EcoRI (117 bp), Mval (152 bp), AccIII (165 bp), NspV (249 bp), SalI (275 bp), BamHI (300 bp) and HinfI (485 bp), and hybridizing under conditions wherein single stranded DNA having the nucleotide sequence of (c) is fixed on a filter and then the filter is incubated with a probe having the nucleotide sequence of (a) or (b) at about 40° C. to about 50° C. for about 10 hours to about 20 hours to cause hybridization.

3. An isolated cytoplasmic male sterility mitochondria gene obtainable by a PCR process using a genomic DNA extracted from a tissue or a cultured cell of carrot of a cytoplasmic male sterility line as a template and oligonucleotide primers according to SEQ ID NO: 15 and SEQ ID NO:12, wherein said PCR process is conducted under conditions such that about 20 to about 40 cycles are carried out in a buffer solution for amplification which includes said primers, a heat resistant DNA polymerase, dNTPs, said genomic DNA and about 1.0 mM to about 4.0 mM magnesium chloride, and wherein the denaturation step is carried out at about 90° C. to about 1 minute to about 3 minutes, the annealing step is carried out at about 50° C. to about 60° C.

for about 1 minute to about 3 minutes, and the elongation step is carried out at about 70° C. to about 73° C. for about 1 minute to about 4 minutes.

4. A plasmid containing the cytoplasmic male sterility mitochondria gene as defined in claim 1, 2 or 3.

5. A microorganism comprising the plasmid as defined in claim 4.

6. A plant cell transformed by introducing the cytoplasmic male sterility DNA as defined in claim 1, 2 or 3.

7. A plant transformed by introducing the cytoplasmic male sterility mitochondria gene as defined in claim 1, 2 or 3.

8. The isolated cytoplasmic male sterility mitochondria gene according to claim 3, wherein the buffer solution contains about 1.5 mM to about 3.0 mM magnesium chloride, the denaturation step is carried out at about 94° C. to about 95° C. for about 1 minute to about 2 minutes, the annealing step is carried out at about 50° C. to about 60° C. for about 1 minute to about 2 minutes, and the elongation step is carried out at about 72° C. to about 73° C. for about 2 minute to about 3 minutes.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 171 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: CDS
        (B) LOCATION: 1..171

(xi) SEQUENCE DESCRIPTION: SEQ ID NO:1:

```
TAT GAC TCC TTC TTT CAC TTC TGG ATC GAC GAA ACA GTC CTA GAT CCA         48
Tyr Asp Ser Phe Phe His Phe Trp Ile Asp Glu Thr Val Leu Asp Pro
 1               5                  10                  15

ACC TGT TTT CAA AGG AGA GAA CGA CCA CCT AGA ACT TCA AGT CAT AAT         96
Thr Cys Phe Gln Arg Arg Glu Arg Pro Pro Arg Thr Ser Ser His Asn
                20                  25                  30

AAA AAC CAT AGA ACC ATA CCT CCG GCT TCC ATT CTT CTC GCT CCA            144
Lys Lys Asn His Arg Thr Ile Pro Pro Ala Ser Ile Leu Leu Ala Pro
            35                  40                  45

TTT TTA ACG GAA AAA AAT TCA AAA TAG                                    171
Phe Leu Thr Glu Lys Asn Ser Lys *
    50                  55
```

(2) INFORMATION FOR SEQ ID NO:2:

(i) SEQUENCE CHARACTERISTICS:
        (A) LENGTH: 57 amino acids
        (B) TYPE: amino acid
        (D) TOPOLOGY: linear (ii) MOLECULE TYPE: protein (xi) SEQUENCE DESCRIPTION: SEQ ID NO:2:

```
Tyr Asp Ser Phe Phe His Phe Trp Ile Asp Glu Thr Val Leu Asp Pro
 1               5                  10                  15

Thr Cys Phe Gln Arg Arg Glu Arg Pro Pro Arg Thr Ser Ser His Asn
                20                  25                  30

Lys Lys Asn His Arg Thr Ile Pro Pro Ala Ser Ile Leu Leu Ala Pro
            35                  40                  45

Phe Leu Thr Glu Lys Asn Ser Lys
    50                  55
```

(2) INFORMATION FOR SEQ ID NO:3:

(i) SEQUENCE CHARACTERISTICS:
        (A) LENGTH: 651 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: CDS
        (B) LOCATION: 1..651

(xi) SEQUENCE DESCRIPTION: SEQ ID NO:3:

```
ATG CCT CAA CTG GAT AAA TTC ACT TAT TTC ACA CAA TTC TTC TGG TCA         48
Met Pro Gln Leu Asp Lys Phe Thr Tyr Phe Thr Gln Phe Phe Trp Ser
 1               5                  10                  15

TGC CTT TTC CTC TTT ACT TTC TAT ATT GCC ATA TGG AAT GAT GGA GAT         96
```

```
                                                                                        -continued Cys Leu Phe Leu Phe Thr Phe Tyr Ile Ala Ile Trp Asn Asp Gly Asp
             20                  25                  30

GGA CTA CTT GGG ATC AGC AGA ATT CTA AAA CTG CGG AAC CAA CTT CTT          144
Gly Leu Leu Gly Ile Ser Arg Ile Leu Lys Leu Arg Asn Gln Leu Leu
             35                  40                  45

TCA CAC CAG GAG AAC AAC ATC CGG AGC AAG GAC CCC AAC AGT TTG GAA          192
Ser His Gln Glu Asn Asn Ile Arg Ser Lys Asp Pro Asn Ser Leu Glu
 50                  55                  60

GAT ATC TTG AGA AAA GGT TTT AGC ACC GGT GTA TCC TAT ATG TAC TCC          240
Asp Ile Leu Arg Lys Gly Phe Ser Thr Gly Val Ser Tyr Met Tyr Ser
 65                  70                  75                  80

AGT TTA TTC GAA GTA TCC CAA TGG TGT AAC GCC GTC GAC TTA TTG GGA          288
Ser Leu Phe Glu Val Ser Gln Trp Cys Asn Ala Val Asp Leu Leu Gly
             85                  90                  95

AAA AGG AGG AGG ATC CCT TTG ATC TCT TGT TTC GGA GAA ATA AGT GGC          336
Lys Arg Arg Arg Ile Pro Leu Ile Ser Cys Phe Gly Glu Ile Ser Gly
            100                 105                 110

TCA CGA GGA ATG GAA AGA AAC ATA TTA TAT TTG ATC TCG AAG TCC TCA          384
Ser Arg Gly Met Glu Arg Asn Ile Leu Tyr Leu Ile Ser Lys Ser Ser
            115                 120                 125

TAT AGC ACT TCT TCC AAT CCT GGA TGG GGG ATC ACT TGT AGG AAT GAC          432
Tyr Ser Thr Ser Ser Asn Pro Gly Trp Gly Ile Thr Cys Arg Asn Asp
130                 135                 140

ATA ACG CTA ATC CAT GTT CCA CAC GGC CAA AGA AGC TTC GAT GGA TTA          480
Ile Thr Leu Ile His Val Pro His Gly Gln Arg Ser Phe Asp Gly Leu
145                 150                 155                 160

TAT GAC TCC TTC TTT CAC TTC TGG ATC GAC GAA ACA GTC CTA GAT CCA          528
Tyr Asp Ser Phe Phe His Phe Trp Ile Asp Glu Thr Val Leu Asp Pro
                165                 170                 175

ACC TGT TTT CAA AGG AGA GAA CGA CCA CCT AGA ACT TCA AGT CAT AAT          576
Thr Cys Phe Gln Arg Arg Glu Arg Pro Pro Arg Thr Ser Ser His Asn
            180                 185                 190

AAA AAA AAC CAT AGA ACC ATA CCT CCG GCT TCC ATT CTT CTC GCT CCA          624
Lys Lys Asn His Arg Thr Ile Pro Pro Ala Ser Ile Leu Leu Ala Pro
            195                 200                 205

TTT TTA ACG GAA AAA AAT TCA AAA TAG                                      651
Phe Leu Thr Glu Lys Asn Ser Lys  *
            210                 215

(2) INFORMATION FOR SEQ ID NO:4:

(i) SEQUENCE CHARACTERISTICS:
        (A) LENGTH:  217 amino acids
        (B) TYPE: amino acid
        (D) TOPOLOGY: linear (ii) MOLECULE TYPE: protein (xi) SEQUENCE DESCRIPTION: SEQ ID NO:4:

Met Pro Gln Leu Asp Lys Phe Thr Tyr Phe Thr Gln Phe Phe Trp Ser
 1                   5                  10                  15

Cys Leu Phe Leu Phe Thr Phe Tyr Ile Ala Ile Trp Asn Asp Gly Asp
             20                  25                  30

Gly Leu Leu Gly Ile Ser Arg Ile Leu Lys Leu Arg Asn Gln Leu Leu
             35                  40                  45

Ser His Gln Glu Asn Asn Ile Arg Ser Lys Asp Pro Asn Ser Leu Glu
 50                  55                  60

Asp Ile Leu Arg Lys Gly Phe Ser Thr Gly Val Ser Tyr Met Tyr Ser
 65                  70                  75                  80

Ser Leu Phe Glu Val Ser Gln Trp Cys Asn Ala Val Asp Leu Leu Gly
             85                  90                  95
```

```
Lys Arg Arg Arg Ile Pro Leu Ile Ser Cys Phe Gly Glu Ile Ser Gly
            100                 105                 110

Ser Arg Gly Met Glu Arg Asn Ile Leu Tyr Leu Ile Ser Lys Ser Ser
        115                 120                 125

Tyr Ser Thr Ser Ser Asn Pro Gly Trp Gly Ile Thr Cys Arg Asn Asp
    130                 135                 140

Ile Thr Leu Ile His Val Pro His Gly Gln Arg Ser Phe Asp Gly Leu
145                 150                 155                 160

Tyr Asp Ser Phe Phe His Phe Trp Ile Asp Glu Thr Val Leu Asp Pro
                165                 170                 175

Thr Cys Phe Gln Arg Arg Glu Arg Pro Pro Arg Thr Ser Ser His Asn
            180                 185                 190

Lys Lys Asn His Arg Thr Ile Pro Pro Ala Ser Ile Leu Leu Ala Pro
        195                 200                 205

Phe Leu Thr Glu Lys Asn Ser Lys
    210                 215

(2) INFORMATION FOR SEQ ID NO:5:

(i) SEQUENCE CHARACTERISTICS:
        (A) LENGTH: 480 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: CDS
        (B) LOCATION: 1..480

(xi) SEQUENCE DESCRIPTION: SEQ ID NO:5:

ATG CCT CAA CTG GAT AAA TTC ACT TAT TTC ACA CAA TTC TTC TGG TCA      48
Met Pro Gln Leu Asp Lys Phe Thr Tyr Phe Thr Gln Phe Phe Trp Ser
1               5                   10                  15

TGC CTT TTC CTC TTT ACT TTC TAT ATT GCC ATA TGC AAT GAT GGA GAT      96
Cys Leu Phe Leu Phe Thr Phe Tyr Ile Ala Ile Cys Asn Asp Gly Asp
            20                  25                  30

GGA CTA CTT GGG ATC AGC AGA ATT CTA AAA CTG CGG AAC CAA CTT CTT     144
Gly Leu Leu Gly Ile Ser Arg Ile Leu Lys Leu Arg Asn Gln Leu Leu
        35                  40                  45

TCA CAC CAG GAG AAC AAC ATC CGG AGC AAG GAC CCC AAC AGT TTG GAA     192
Ser His Gln Glu Asn Asn Ile Arg Ser Lys Asp Pro Asn Ser Leu Glu
    50                  55                  60

GAT ATC TTG AGA AAA GGT TTT AGC ACC GGT GTA TCC TAT ATG TAC TCC     240
Asp Ile Leu Arg Lys Gly Phe Ser Thr Gly Val Ser Tyr Met Tyr Ser
65                  70                  75                  80

AGT TTA TTC GAA GTA TCC CAA TGG TGT AAC GCC GTC GAC TTA TTG GGA     288
Ser Leu Phe Glu Val Ser Gln Trp Cys Asn Ala Val Asp Leu Leu Gly
                85                  90                  95

AAA AGG AGG AGG ATC CCT TTG ATC TCT TGT TTC GGA GAA ATA AGT GGC     336
Lys Arg Arg Arg Ile Pro Leu Ile Ser Cys Phe Gly Glu Ile Ser Gly
            100                 105                 110

TCA CGA GGA ATG GAA AGA AAC ATA TTC TAT TTG ATC TCG AAG TCC TCA     384
Ser Arg Gly Met Glu Arg Asn Ile Phe Tyr Leu Ile Ser Lys Ser Ser
        115                 120                 125

TAT AGC ACT TCT TCC AAT CCT GGA TGG GGG ATC ACT TGT AGG AAT GAC     432
Tyr Ser Thr Ser Ser Asn Pro Gly Trp Gly Ile Thr Cys Arg Asn Asp
    130                 135                 140

ATA ACG CTA ATC CAT GTT CCA CAC GGC CAA GGA AGC ATC GGT TTT TAA     480
Ile Thr Leu Ile His Val Pro His Gly Gln Gly Ser Ile Gly Phe  *
145                 150                 155
```

145              150              155              160

(2) INFORMATION FOR SEQ ID NO:6:

(i) SEQUENCE CHARACTERISTICS:
       (A) LENGTH: 160 amino acids
       (B) TYPE: amino acid
       (D) TOPOLOGY: linear (ii) MOLECULE TYPE: protein (xi) SEQUENCE DESCRIPTION: SEQ ID NO:6:

Met Pro Gln Leu Asp Lys Phe Thr Tyr Phe Thr Gln Phe Phe Trp Ser
 1               5                  10                  15

Cys Leu Phe Leu Phe Thr Phe Tyr Ile Ala Ile Cys Asn Asp Gly Asp
                20                  25                  30

Gly Leu Leu Gly Ile Ser Arg Ile Leu Lys Leu Arg Asn Gln Leu Leu
            35                  40                  45

Ser His Gln Glu Asn Asn Ile Arg Ser Lys Asp Pro Asn Ser Leu Glu
        50                  55                  60

Asp Ile Leu Arg Lys Gly Phe Ser Thr Gly Val Ser Tyr Met Tyr Ser
65                  70                  75                  80

Ser Leu Phe Glu Val Ser Gln Trp Cys Asn Ala Val Asp Leu Leu Gly
                85                  90                  95

Lys Arg Arg Arg Ile Pro Leu Ile Ser Cys Phe Gly Glu Ile Ser Gly
                100                 105                 110

Ser Arg Gly Met Glu Arg Asn Ile Phe Tyr Leu Ile Ser Lys Ser Ser
            115                 120                 125

Tyr Ser Thr Ser Ser Asn Pro Gly Trp Gly Ile Thr Cys Arg Asn Asp
130                 135                 140

Ile Thr Leu Ile His Val Pro His Gly Gln Gly Ser Ile Gly Phe
145                 150                 155                 160

(2) INFORMATION FOR SEQ ID NO:7:

(i) SEQUENCE CHARACTERISTICS:
       (A) LENGTH: 1193 base pairs
       (B) TYPE: nucleic acid
       (C) STRANDEDNESS: double
       (D) TOPOLOGY: linear (ii) MOLECULE TYPE: other nucleic acid (ix) FEATURE:
       (A) NAME/KEY: CDS
       (B) LOCATION: 1..651

(xi) SEQUENCE DESCRIPTION: SEQ ID NO:7:

```
ATG CCT CAA CTG GAT AAA TTC ACT TAT TTC ACA CAA TTC TTC TGG TCA        48
Met Pro Gln Leu Asp Lys Phe Thr Tyr Phe Thr Gln Phe Phe Trp Ser
 1               5                  10                  15

TGC CTT TTC CTC TTT ACT TTC TAT ATT GCC ATA TGG AAT GAT GGA GAT        96
Cys Leu Phe Leu Phe Thr Phe Tyr Ile Ala Ile Trp Asn Asp Gly Asp
                20                  25                  30

GGA CTA CTT GGG ATC AGC AGA ATT CTA AAA CTG CGG AAC CAA CTT CTT       144
Gly Leu Leu Gly Ile Ser Arg Ile Leu Lys Leu Arg Asn Gln Leu Leu
            35                  40                  45

TCA CAC CAG GAG AAC AAC ATC CGG AGC AAG GAC CCC AAC AGT TTG GAA       192
Ser His Gln Glu Asn Asn Ile Arg Ser Lys Asp Pro Asn Ser Leu Glu
        50                  55                  60

GAT ATC TTG AGA AAA GGT TTT AGC ACC GGT GTA TCC TAT ATG TAC TCC       240
Asp Ile Leu Arg Lys Gly Phe Ser Thr Gly Val Ser Tyr Met Tyr Ser
65                  70                  75                  80
```

```
AGT TTA TTC GAA GTA TCC CAA TGG TGT AAC GCC GTC GAC TTA TTG GGA        288
Ser Leu Phe Glu Val Ser Gln Trp Cys Asn Ala Val Asp Leu Leu Gly
                85                  90                  95

AAA AGG AGG AGG ATC CCT TTG ATC TCT TGT TTC GGA GAA ATA AGT GGC        336
Lys Arg Arg Arg Ile Pro Leu Ile Ser Cys Phe Gly Glu Ile Ser Gly
            100                 105                 110

TCA CGA GGA ATG GAA AGA AAC ATA TTA TAT TTG ATC TCG AAG TCC TCA        384
Ser Arg Gly Met Glu Arg Asn Ile Leu Tyr Leu Ile Ser Lys Ser Ser
        115                 120                 125

TAT AGC ACT TCT TCC AAT CCT GGA TGG GGG ATC ACT TGT AGG AAT GAC        432
Tyr Ser Thr Ser Ser Asn Pro Gly Trp Gly Ile Thr Cys Arg Asn Asp
    130                 135                 140

ATA ACG CTA ATC CAT GTT CCA CAC GGC CAA AGA AGC TTC GAT GGA TTA        480
Ile Thr Leu Ile His Val Pro His Gly Gln Arg Ser Phe Asp Gly Leu
145                 150                 155                 160

TAT GAC TCC TTC TTT CAC TTC TGG ATC GAC GAA ACA GTC CTA GAT CCA        528
Tyr Asp Ser Phe Phe His Phe Trp Ile Asp Glu Thr Val Leu Asp Pro
                165                 170                 175

ACC TGT TTT CAA AGG AGA GAA CGA CCA CCT AGA ACT TCA AGT CAT AAT        576
Thr Cys Phe Gln Arg Arg Glu Arg Pro Pro Arg Thr Ser Ser His Asn
            180                 185                 190

AAA AAA AAC CAT AGA ACC ATA CCT CCG GCT TCC ATT CTT CTC GCT CCA        624
Lys Lys Asn His Arg Thr Ile Pro Pro Ala Ser Ile Leu Leu Ala Pro
        195                 200                 205

TTT TTA ACG GAA AAA AAT TCA AAA TAG AGTCTATATC GAATATTGCA              671
Phe Leu Thr Glu Lys Asn Ser Lys  *
    210                 215

AGCTTATAGA TTGATAGAAC TACAAGGGTC TGATTCTTCT GAATAAGATG ATATGATATG      731
TAGGTAGTTC GGTGTTTCTA GCCGGATGCG ACCCCCCACG AATACAGTAT TGTCTCAGCT      791
GAAGCGCCTC TTAGAGTATA TAATCTTGAG GCGAGAGGTG TAAGCATCGC GAGATGTTCA      851
GCCATCTCGT ACTAAAAAAA GAAAAGCTTG TGGGGATCAT AGTCTCTGCC ATGTCTTAGG      911
GCTTATGCCC AAGCACGATG AATAGAGGCA TTCTCTGAGT AGACGCGGTG TAATGACAAA      971
ACAAAAGCAA AATTGACGAA AATGACGTGT CATGTTAGAA GGAATGAAAT TAATTGGAGC     1031
CGGTGCAGCA ACAATTGCTT TAGCTGGAGC AGCCATTGGT ATTGGAAACG TTTTCAGTTC     1091
TTTGATTCAT TCCGTGGCGC GAAATCCATC TTTGGCGAAA CAATTATTTG GTTGTTAATG     1151
GCAACAAAAT AAAAAGCATC GAGAAAGGTC TACTTGCTTG CC                       1193

(2) INFORMATION FOR SEQ ID NO:8:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:8:

Met Pro Gln Leu Asp Lys Phe Thr Tyr Phe Thr Gln Phe Phe Trp Ser
1               5                   10                  15

Cys Leu Phe Leu Phe Thr Phe Tyr Ile Ala Ile Trp Asn Asp Gly Asp
            20                  25                  30

Gly Leu Leu Gly Ile Ser Arg Ile Leu Lys Leu Arg Asn Gln Leu Leu
        35                  40                  45

Ser His Gln Glu Asn Asn Ile Arg Ser Lys Asp Pro Asn Ser Leu Glu
    50                  55                  60

Asp Ile Leu Arg Lys Gly Phe Ser Thr Gly Val Ser Tyr Met Tyr Ser
```

```
              65                   70                   75                    80
Ser Leu Phe Glu Val Ser Gln Trp Cys Asn Ala Val Asp Leu Leu Gly
                         85                     90                     95

Lys Arg Arg Arg Ile Pro Leu Ile Ser Cys Phe Gly Glu Ile Ser Gly
                100                    105                    110

Ser Arg Gly Met Glu Arg Asn Ile Leu Tyr Leu Ile Ser Lys Ser Ser
                115                    120                    125

Tyr Ser Thr Ser Ser Asn Pro Gly Trp Gly Ile Thr Cys Arg Asn Asp
            130                    135                    140

Ile Thr Leu Ile His Val Pro His Gly Gln Arg Ser Phe Asp Gly Leu
145                    150                    155                    160

Tyr Asp Ser Phe Phe His Phe Trp Ile Asp Glu Thr Val Leu Asp Pro
                    165                    170                    175

Thr Cys Phe Gln Arg Arg Glu Arg Pro Pro Arg Thr Ser Ser His Asn
                180                    185                    190

Lys Lys Asn His Arg Thr Ile Pro Pro Ala Ser Ile Leu Leu Ala Pro
                195                    200                    205

Phe Leu Thr Glu Lys Asn Ser Lys
        210                    215

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:9:

TATGACTCCT TCTTTCACTT                                                      20

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: other nucleic acid
        (A) DESCRIPTION: /desc = "Primer"

(ix) FEATURE:
        (A) NAME/KEY: modified_base
        (B) LOCATION: 14
        (D) OTHER INFORMATION: /mod_base= i (xi) SEQUENCE DESCRIPTION: SEQ ID NO:10:

CTATTTTGAA TTTNTTTCCG T                                                    21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:11:
```

```
TATGACTCCT TCTTTCACTT T                                                      21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:12:

CTATTTTGAA TTTTTTTCCG T                                                      21

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:13:

CTGGATCGAC GAAACAGTCC                                                        20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:14:

TAAAAATGGA GCGAGAAGAA                                                        20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:15:

ATGCCTCAAC TGGATAAATT                                                        20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:16:
```

```
TTAAAAACCG ATGCTTCCTT                                                      20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer"

(xi) SEQUENCE DESCRIPTION: SEQ ID NO:17:

CTATTTTGAA TTTTTTTCCG                                                      20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer"

(xi) SEQUENCE DESCRIPTION: SEQ ID NO:18:

ATAACGCTAA TCCATGTTCC A                                                    21

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer"

(xi) SEQUENCE DESCRIPTION: SEQ ID NO:19:

GCTTGCAATA TTCGATATAG                                                      20
```